United States Patent
Maloney et al.

(10) Patent No.: US 11,000,415 B2
(45) Date of Patent: May 11, 2021

(54) SEALING ASSEMBLY FOR INFLATABLE IN-EAR DEVICE

(71) Applicant: EERS GLOBAL TECHNOLOGIES INC., Montréal (CA)

(72) Inventors: Michael Maloney, Caledon (CA); Michael C. Turcot, Montréal (CA)

(73) Assignee: EERS GLOBAL TECHNOLOGIES INC., Montreal (CA)

( * ) Notice: Subject to any disclaimer, the term of this patent is extended or adjusted under 35 U.S.C. 154(b) by 329 days.

(21) Appl. No.: 16/004,413

(22) Filed: Jun. 10, 2018

(65) Prior Publication Data

US 2018/0289549 A1    Oct. 11, 2018

Related U.S. Application Data

(63) Continuation-in-part of application No. 12/923,697, filed on Oct. 5, 2010, now abandoned.

(60) Provisional application No. 61/272,533, filed on Oct. 5, 2009.

(51) Int. Cl.
| | |
|---|---|
| *A61F 11/00* | (2006.01) |
| *A61F 11/10* | (2006.01) |
| *H04R 25/00* | (2006.01) |
| *A61F 11/08* | (2006.01) |
| *H04R 1/10* | (2006.01) |

(52) U.S. Cl.
CPC ............ *A61F 11/10* (2013.01); *H04R 25/656* (2013.01); *A61F 2011/085* (2013.01); *H04R 1/1016* (2013.01); *H04R 2225/023* (2013.01)

(58) Field of Classification Search
CPC .......... A61F 11/06; A61F 11/08; A61F 11/10; A61F 2011/085; A61F 11/12; H04R 25/652; H04R 2460/17; H04R 25/65; H04R 2460/09; H04R 2460/15; H04R 25/658; H04R 25/659; H04R 25/656
See application file for complete search history.

(56) References Cited

U.S. PATENT DOCUMENTS

| | | | | |
|---|---|---|---|---|
| 2,803,308 | A * | 8/1957 | Di Mattia | ................ A61B 7/02 |
| | | | | 181/135 |
| 4,190,033 | A * | 2/1980 | Foti | ...................... A61B 5/4863 |
| | | | | 128/865 |
| 6,339,648 | B1 | 1/2002 | McIntosh et al. | |
| 6,513,621 | B1 | 2/2003 | Deslauriers et al. | |

(Continued)

FOREIGN PATENT DOCUMENTS

| | | |
|---|---|---|
| WO | 2008/070986 A1 | 6/2008 |
| WO | 2009/077902 A2 | 6/2009 |

*Primary Examiner* — Victoria J Hicks
(74) *Attorney, Agent, or Firm* — Praxis

(57) ABSTRACT

An inflatable in-ear device includes a core member with a platform provided with a sealing assembly in the form of a locating recess for the registration of a retention ring formed around a defining opening of a sheath arranged in close circumjacent manner around the platform attached to the core member, an abutment surface being formed on a capping for the platform and the core member whereby in use positive location of the retention ring within the recess is achieved by the closure of the recess by the abutment surface. A space is defined between the sheath and the core member for the injection of a settable material used for the inflation of the sheath once the device is emplaced within the ear canal of the ear.

9 Claims, 3 Drawing Sheets

(56) References Cited

U.S. PATENT DOCUMENTS

| | | | |
|---|---|---|---|
| 6,687,377 B2 | 2/2004 | Voix et al. | |
| 6,754,357 B2 | 6/2004 | McIntosh et al. | |
| 7,418,105 B2 * | 8/2008 | McIntosh | H04R 25/658 |
| | | | 381/322 |
| 7,864,972 B2 * | 1/2011 | McIntosh | A61F 11/08 |
| | | | 381/322 |
| 2002/0114479 A1 | 8/2002 | McIntoch et al. | |
| 2005/0123146 A1 | 6/2005 | Voix et al. | |

* cited by examiner

SEALING ASSEMBLY FOR INFLATABLE IN-EAR DEVICE

CROSS REFERENCE TO RELATED APPLICATIONS

The present application is a Continuation-In-Part (C.I.P.) of parent patent application Ser. No. 12/923,697 filed on Oct. 5, 2010 which claims benefit of U.S. Provisional Application for Patent Ser. No. 61/272,533 filed on Oct. 5, 2009, both of which being incorporated herein by reference.

FIELD OF THE INVENTION

The present invention concerns an inflatable in-ear device and in particular has reference to a component thereof for sealing the device during its inflation.

In-ear devices include intra-aural hearing protectors (earplugs), earphones, hearing-aid devices and the like and the invention relates to custom-fitting in-ear devices that are formed in situ to conform morphologically to the inside of the ear canal and the cavum concha of the individual.

BACKGROUND OF THE INVENTION

The present inventors have proposed hearing protection devices which offer custom-fitting to the ear of the individual and are exemplified and claimed in U.S. Pat. Nos. 6,339,648 and 6,754,357 to McIntosh et al. Principally, these devices comprise a core member around which is arranged a sheath in a deflated state, a permanent setting compound being injected into the cavity defined between the core member and the sheath to bring the device into morphological conformity to the contours of the ear canal. In this way, the in-ear device is produced in customized fashion thus enhancing the performance thereof and indeed the comfort of the individual. These devices require a bonding of the open end of the sheath to the core member in order to seal off and ensure that the sheath remains in place and sealed during injection of the settable compound that stretches the sheath.

One of the problems associated with the formation of the in situ device in terms of the injection of the setting compound is to ensure a proper locking and sealing of the core member and the sheath to prevent inadvertent leakage.

There is thus a need to provide an improved sealing assembly for an inflatable in-ear device.

SUMMARY OF THE INVENTION

It is therefore a general object of the present invention to provide an improved sealing assembly for an inflatable in-ear device provided with a novel and inventive feature for locking and sealing the sheath to the core member at least during inflation of the sheath to conform morphologically to the ear canal of the individual.

An advantage of the present invention is that the sealing assembly enables swift and effective location and sealing as between the sheath and the core member prior to inflation of the sheath. A retention ring of the sheath positively engages a locating recess or channel formed in a platform, and an end capping further secures the sheath by closing off the channel.

Another advantage of the present invention is that the sealing assembly has the provision of an end capping for engaging the core member and the sheath, a platform being provided for the core member.

According to an aspect of the present invention there is provided an inflatable in-ear device comprising a core member of generally similar form to the contour of the ear canal of an individual, a sound bore being defined within and through the core member from an exterior region of the core member adapted to be outside of the ear canal to an inner end of the core member adapted to be within the ear canal, a platform to which the core member is attached to being adapted to be outside of the ear canal and defining an external surface thereof being substantially perpendicular to a direction towards the inner end, an inflatable open-ended sheath having a closed end secured to the inner end of the core member, the inflatable open-ended sheath assuming a first inverted condition and being foldable into an inflatable condition in close adjacency to the core member prior to inflation, an open end of the inflatable open-ended sheath being provided with a retention ring, the platform including a locating recess formed therein and extending from the external surface inwardly therein towards the inner end of the core member, the locating recess capturing the retention ring therein in a positive fashion and in sealing registration with the platform and the core member with the inflatable open-ended sheath being folded into the inflatable condition, without requiring any bonding agent.

In one embodiment, the device further includes an exterior end capping being engageable with the platform and having an abutment surface for abutment therewith, the abutment surface forming an enclosure with the locating recess to further secure the retention ring therein.

In one embodiment, the platform is provided with a central boss, the locating recess circumscribing the central boss in annular manner.

In one embodiment, a perimeter of the open end having the retention ring is smaller than that of the locating recess whereby in use placement of the retention ring in the locating recess is achieved by stretching the retention ring for spring engagement within the locating recess.

The registration of the ring on the sheath with the core member is achieved by the provision of a locating recess on the core member into which the ring is positively disposed, and preferably slightly sprung or stretched, for locking and sealing of the sheath to the core member.

Adhesives or other forms of bonding strategies may be used to secure the assembly once the ring is positioned in the recess of the core member.

The platform is provided with an inlet for a settable material employed for the inflation of the sheath and an outlet for the egress of any excess material that may issue from the cavity between the core member and the sheath as a result of full injection of the material. The inlet and the outlet provided in the platform communicate in flow relationship with a corresponding inlet and outlet formed in the core member.

The retention ring tightly and sealably registers with the enclosure in a manner similar to that of an O-ring, with the retention ring being thicker than a remaining portion of the inflatable open-ended sheath.

Other objects and advantages of the present invention will become apparent from a careful reading of the following description.

BRIEF DESCRIPTION OF THE DRAWINGS

Further aspects and advantages of the present invention will become better understood with reference to the description in association with the following figures, in which similar references used in different figures denote similar components, wherein.

DETAILED DESCRIPTION OF THE PREFERRED EMBODIMENTS

Figure 1:
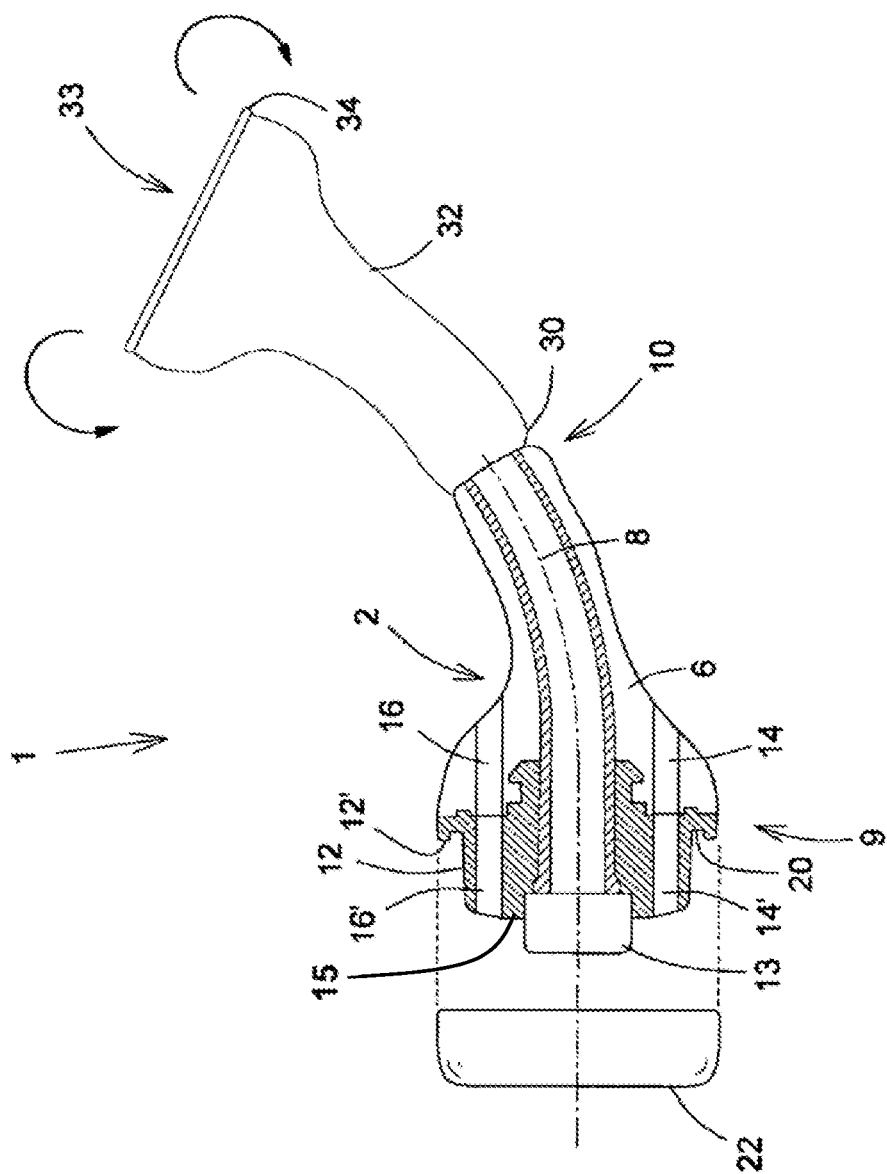
FIG. 1 is a part cross-sectional schematic view of an inflatable in-ear device with a sealing assembly in accordance with an embodiment of the present invention, showing the sheath in a full inverted condition.

Referring to the drawings, there is shown generally at 1 an in-ear device which may be employed as a hearing protection device or as a hearing aid. The device 1 comprises a core member 2 contoured generally to the expected shape of an ear canal 4 (see FIG. 3), the member 2 having a nipple section 6 of for example soft silicone or the like with a sound bore 8 extending from the relatively outer region 9 of the member locatable outside the ear canal 4 to the further end 10, or inner end 10. At the region 9 the core member 2 is mounted in platform 12 having a central boss 15 through which the sound bore 8 also extends as shown with a termination plug 13.

The core member 2 has two passageways 14, 16 which are for the entry and excess discharge respectively of the inflating settable fluid material (not shown). The platform 12 of the core member 2 defines an external surface 12' that is substantially perpendicular to a direction oriented towards the inner end 10. The platform 12 is provided with an annular recess or channel 20 circumscribing the boss 15 of the platform 12 and extending from the external surface 12' inwardly therein towards the inner end 10 of the core member 2. The platform 12 further has two passageways 14', 16' corresponding to and in flow communication with the passageways 14, 16. An end capping 22 is provided for the platform 12 and has a central opening 18 to accept the plug 13 and provide clearance for access to the passageways 14', 16'. The capping 22 has an abutment surface 20' for contacting the recess 20 as a means of retention as described below. Means for locking capping 22 to the platform 12 could include thermal welding or the use of bonding agents or the like, if needed.

At the inner end 10 of the core member 2 there is affixed the closed end 30 of an inflatable sheath 32 which as illustrated in FIG. 1 is inverted, i.e. turned inside out, with its open end 33 shown extended from the core member 2. Its open end 33 is typically characterized by a substantially larger and thicker outer ring 34, or beading or lip for the purpose of registration within the annular recess 20 in a manner similar to that of an O-ring.

Figure 2:
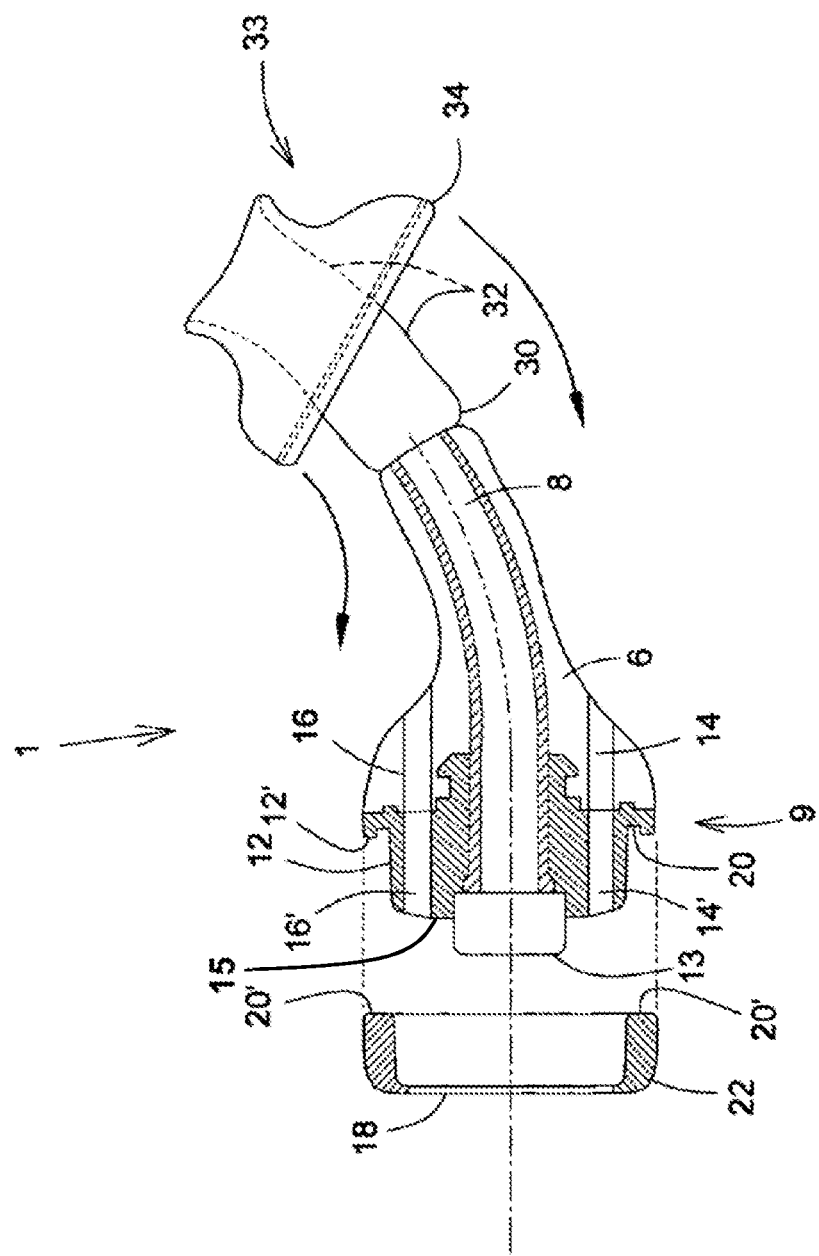
FIG. 2 is a view similar to FIG. 1 with the sheath shown in the process of being folded into close adjacency with the core member.
Figure 3:
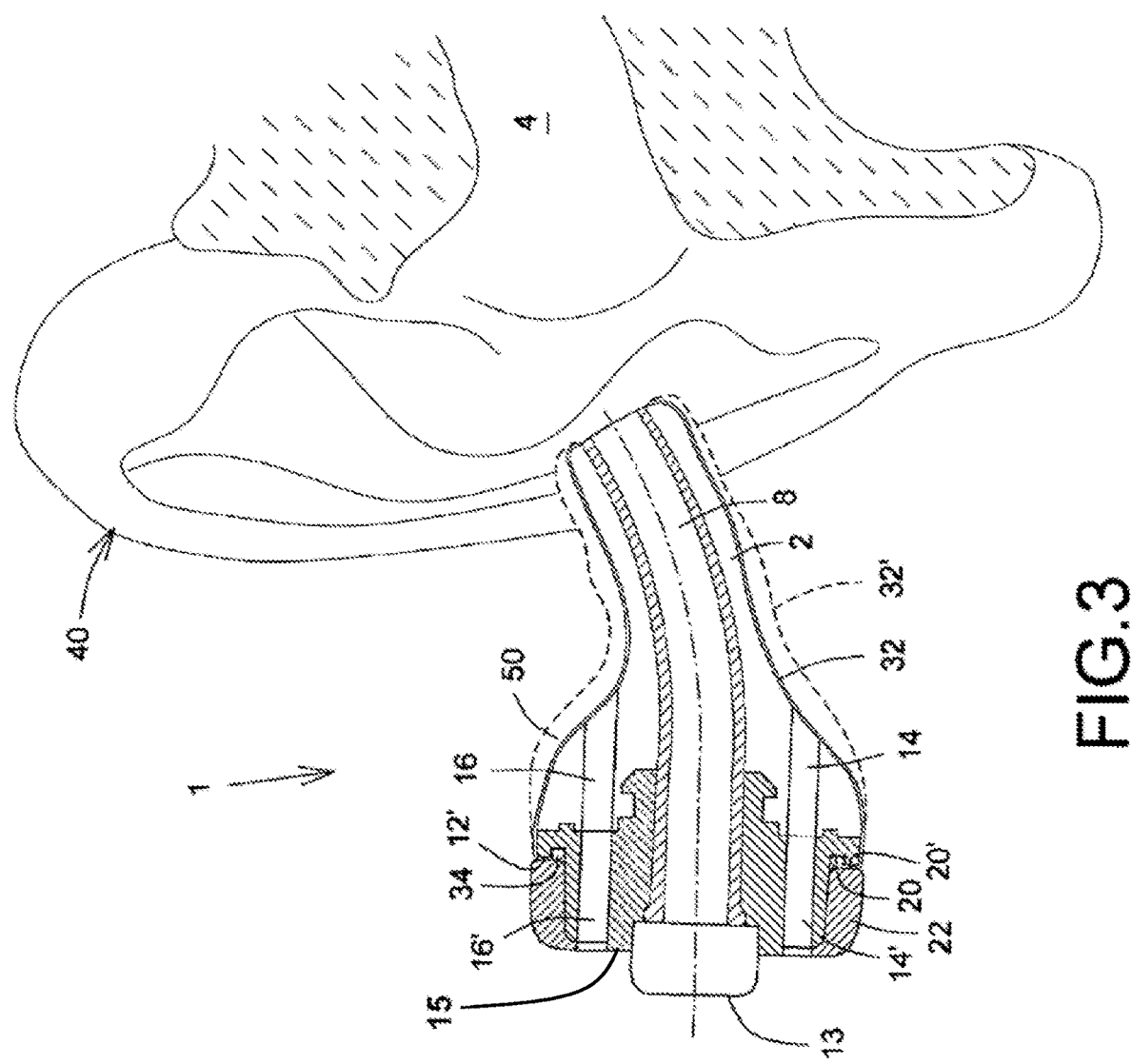
FIG. 3 is a view similar to FIG. 1 with the in-ear device about to be inserted into an ear canal prior to the inflation of the sheath in situ in the ear canal.

In FIG. 2 the sheath 32 is shown being rolled back over the core member 2 in the direction of the arrows and finally assumes the inflatable condition illustrated in FIG. 3 wherein the ring 34 of the sealing assembly has been put into registration within the annular recess 20 to provide a secure location and sealing for the sheath 32, without requiring any bonding agent or the like. Typically, the perimeter of the open end 33 having the retention ring 34 is smaller than the perimeter (or length) of the locating recess 20 such that, in use, the placement of the retention ring 34 in the locating recess 20 is achieved by stretching the retention ring 34 for spring engagement, in a positive fashion, within the locating recess 20. FIG. 3 also shows the application of the end capping 22 over the end of the platform 12 and the core member 2, the abutment surface 20' of the capping having created an enclosure for the annular recess 20 to capture the ring within the recess 20, although additional locking means could be considered (see hereinabove) if desired.

The in-ear device in the condition illustrated in FIG. 3 is ready for insertion into the ear canal 4 of the ear 40, the sheath 32 enveloping the core member 2 to give a space 50 for the injection of an inflation medium (not shown) through the passages 14, 16, 14', 16' once the device has been fully inserted into the canal 4. The injection of the medium effects a customised formation within the canal 4 whereby the inflated sheath 32' conforms morphologically to the shape and contours of the ear canal, as shown in dotted lines. The registration of the ring 34 with the mating surface 20 ensures correct positioning and sealing to ensure prevention of leakage at the point where the sheath 32 meets the core member 2 at its relatively outer end.

Although the channel 20 is shown has having a generally rectangular or square cross-sectional shape, one skilled in the art would readily understand that any other shape could be considered without departing from the scope of the present invention, such as for example, semi-circular, semi-elliptical or triangular.

Although the present invention has been described with a certain degree of particularity, it is to be understood that the disclosure has been made by way of example only and that the present invention is not limited to the features of the embodiments described and illustrated herein, but includes all variations and modifications within the scope and spirit of the invention as hereinafter claimed.

We claim:

1. An inflatable in-ear device comprising a core member of generally similar form to a contour of an ear canal of an individual, a sound bore being defined within and through the core member from an exterior region of the core member adapted to be outside of the ear canal to an inner end of the core member adapted to be within the ear canal, a platform to which the core member is attached to being adapted to be outside of the ear canal and defining an external surface thereof being substantially perpendicular to a direction towards the inner end, an inflatable open-ended sheath having a closed end secured to the inner end of the core member, the inflatable open-ended sheath assuming a first inverted condition and being foldable into an inflatable condition in close adjacency to the core member prior to inflation, an open end of the inflatable open-ended sheath being provided with a retention ring, the platform including a locating channel formed therein and extending from the external surface inwardly therein towards the inner end of the core member, the locating channel retaining the retention ring therein in a positive fashion and in sealing registration with the platform and the core member with the inflatable open-ended sheath being folded into the inflatable condition.

2. An inflatable in-ear device according to claim 1, further including an exterior end capping being engageable with the platform and having an abutment surface for abutment therewith, the abutment surface forming an enclosure with the locating channel to further secure the retention ring therein.

3. An inflatable in-ear device according to claim 2, wherein the retention ring is thicker than a remaining portion of the inflatable open-ended sheath.

4. An inflatable in-ear device according to claim 3, wherein the retention ring tightly and sealably registers with the enclosure in a manner similar to that of an O-ring.

5. An inflatable in-ear device according to claim 1, wherein the platform is provided with a central boss, the locating channel circumscribing the central boss in annular manner.

6. An inflatable in-ear device according to claim 1, wherein a perimeter of the open end having the retention ring is smaller than that of the locating channel whereby in use placement of the retention ring in the locating channel is achieved by stretching the retention ring for spring engagement within the locating channel.

7. An inflatable in-ear device according to claim 1, wherein a bonding agent further secures the retention ring within the locating channel.

8. An inflatable in-ear device according to claim 1, wherein the core member and the platform are provided with communicating inlets and outlets for passage of an inflation medium there through.

9. An inflatable in-ear device according to claim 1, wherein the locating channel has a generally rectangular cross-sectional shape.

\* \* \* \* \*